ABSTRACT
United States Patent [19]
Förster

[11] 4,202,100
[45] May 13, 1980

[54] ORTHODONTIC APPLIANCE

[75] Inventor: Rolf Förster, Pforzheim, Fed. Rep. of Germany

[73] Assignee: Firma Bernhard Förster, Pforzheim, Fed. Rep. of Germany

[21] Appl. No.: 844,379

[22] Filed: Oct. 21, 1977

[30] Foreign Application Priority Data

Oct. 28, 1976 [DE] Fed. Rep. of Germany ....... 2648990
Oct. 5, 1977 [DE] Fed. Rep. of Germany ....... 2744740

[51] Int. Cl.² .............................................. A61C 7/00
[52] U.S. Cl. ......................................... 433/7; 433/4; 433/5; 433/22
[58] Field of Search ............. 24/115 A, 114.5, 129 W; 403/336, 367; 339/103; 32/14 D

[56] References Cited

U.S. PATENT DOCUMENTS

| 2,318,001 | 5/1943 | Linde | 32/14 E |
| 2,910,315 | 10/1959 | Stevens | 403/367 |
| 3,280,688 | 10/1966 | Parkin et al. | 403/344 |
| 3,835,540 | 9/1974 | Biederman | 32/14 D |
| 3,909,945 | 10/1975 | Foxman | 32/14 D |

Primary Examiner—Robert Peshock

[57] ABSTRACT

Force-transmitting means serve to exert a correcting force on at least one tooth of a patient and comprise an elongated first element and at least one second element. At least one clamping sleeve resiliently clamps itself on said first element and engages said second element and has a radially inwardly tapering longitudinal slot, which is adapted to receive an implement which is operable to widen said slot so that said clamping sleeve is slidable along said first element.

22 Claims, 25 Drawing Figures

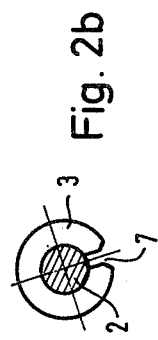
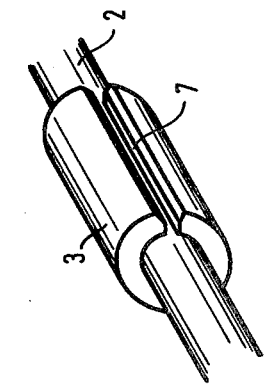
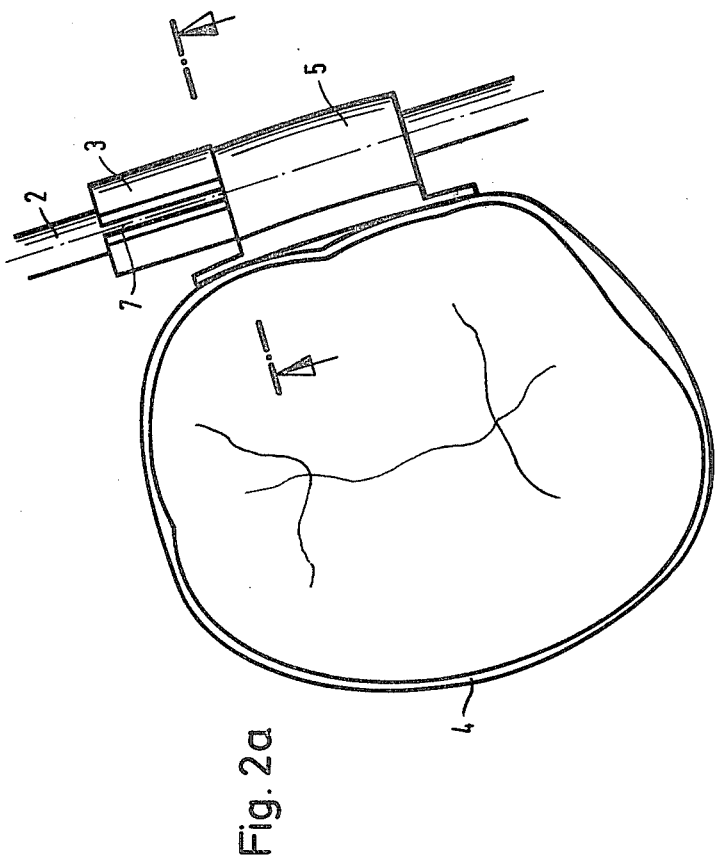

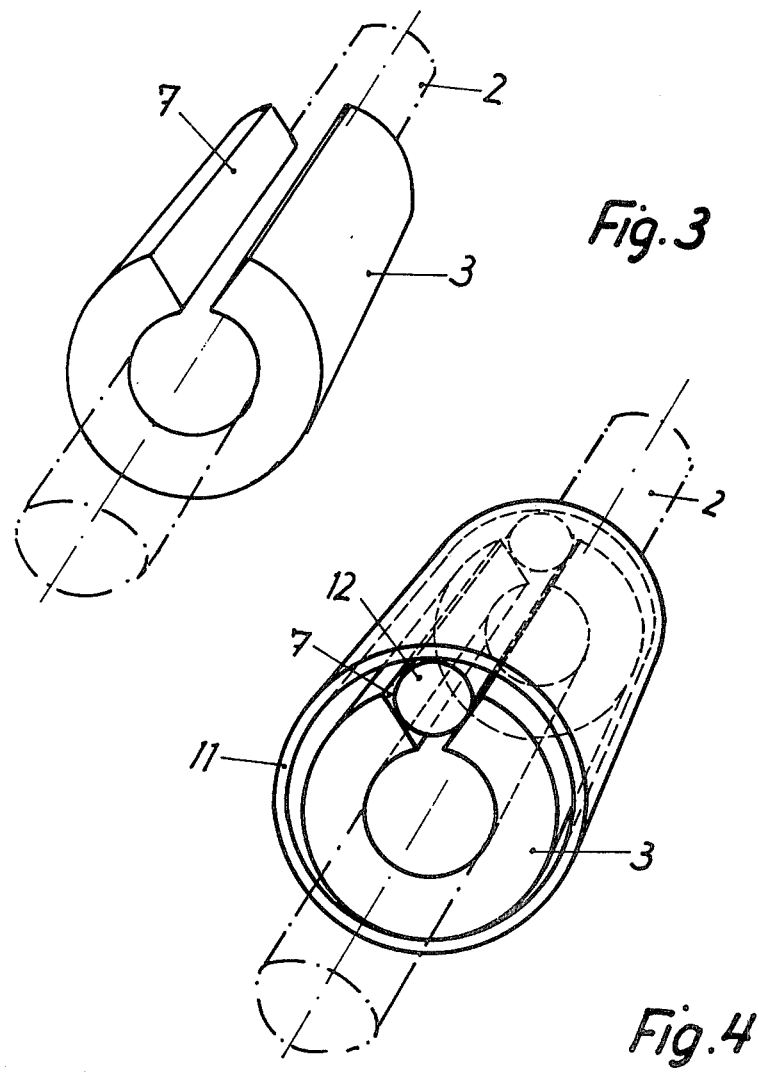

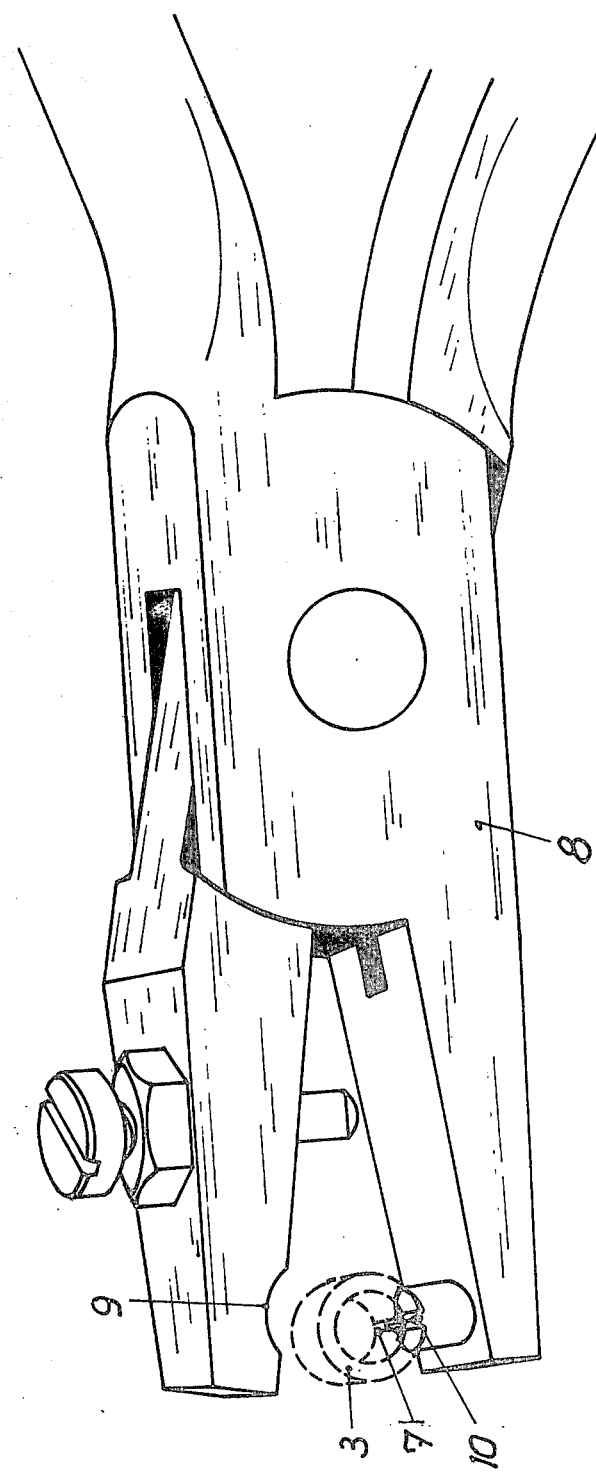

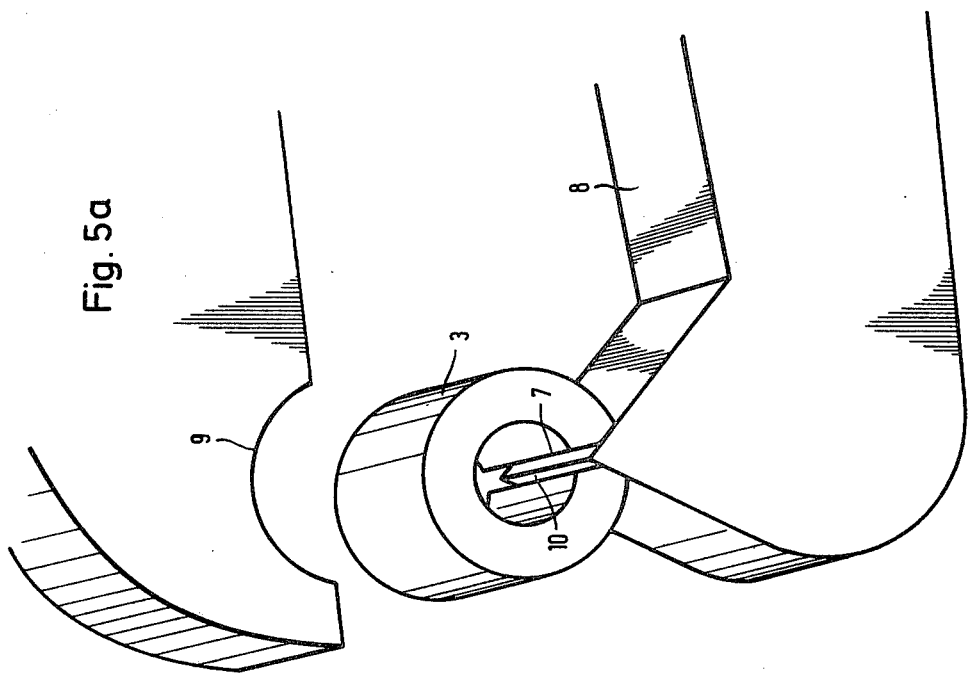
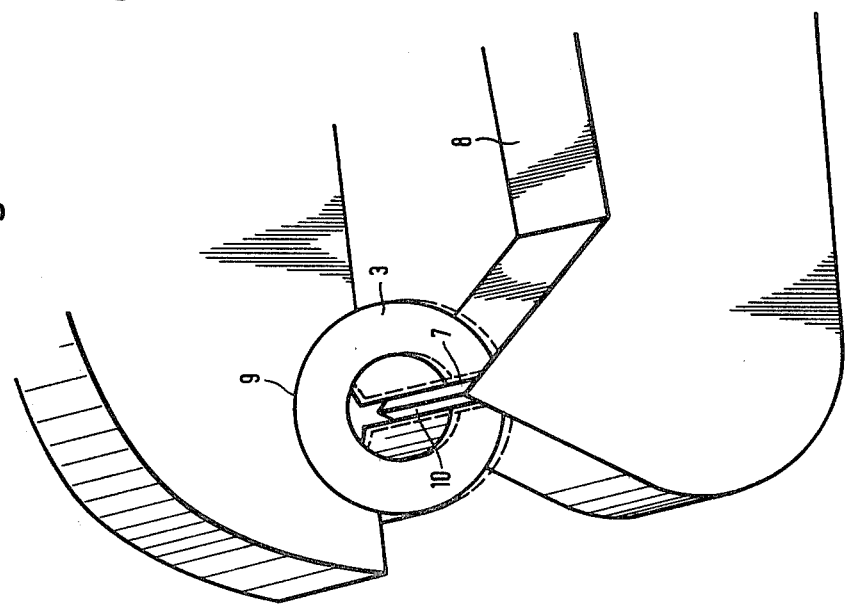

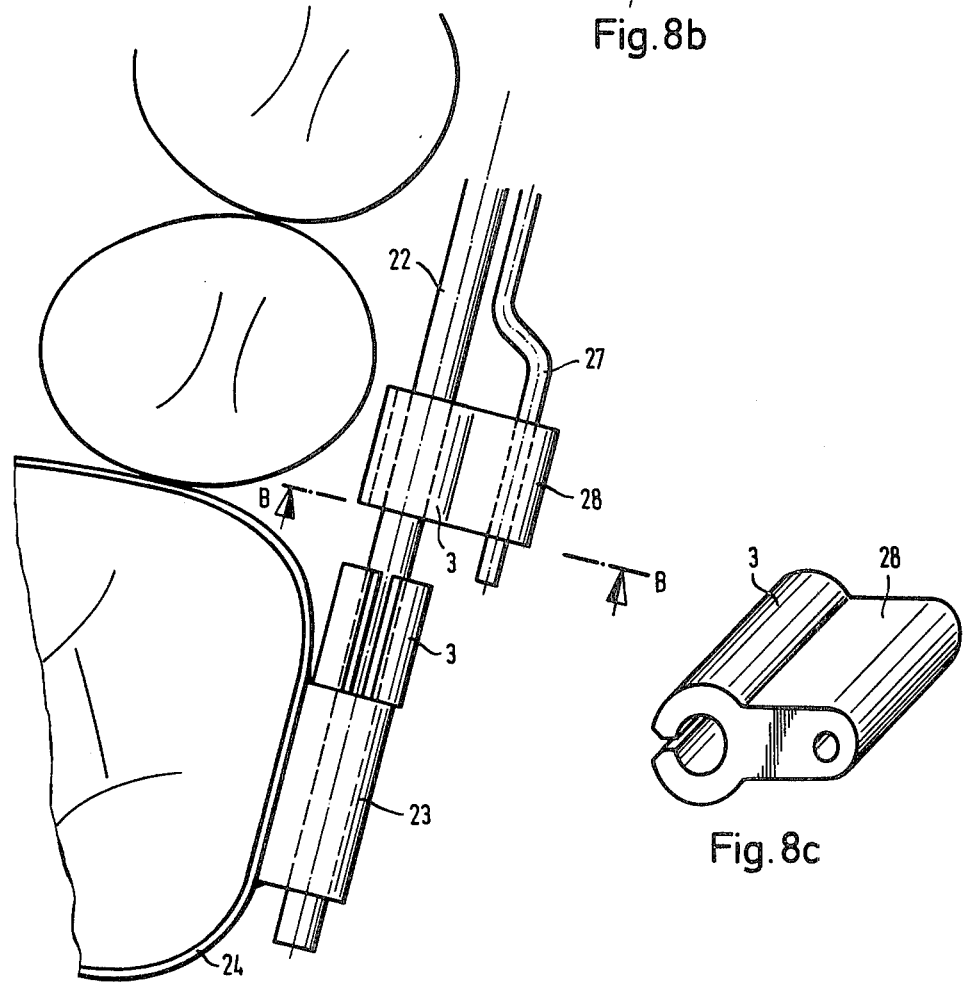

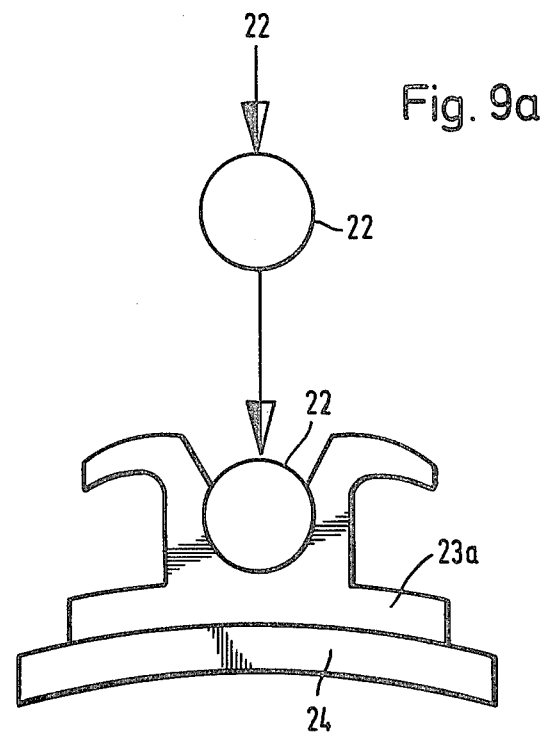

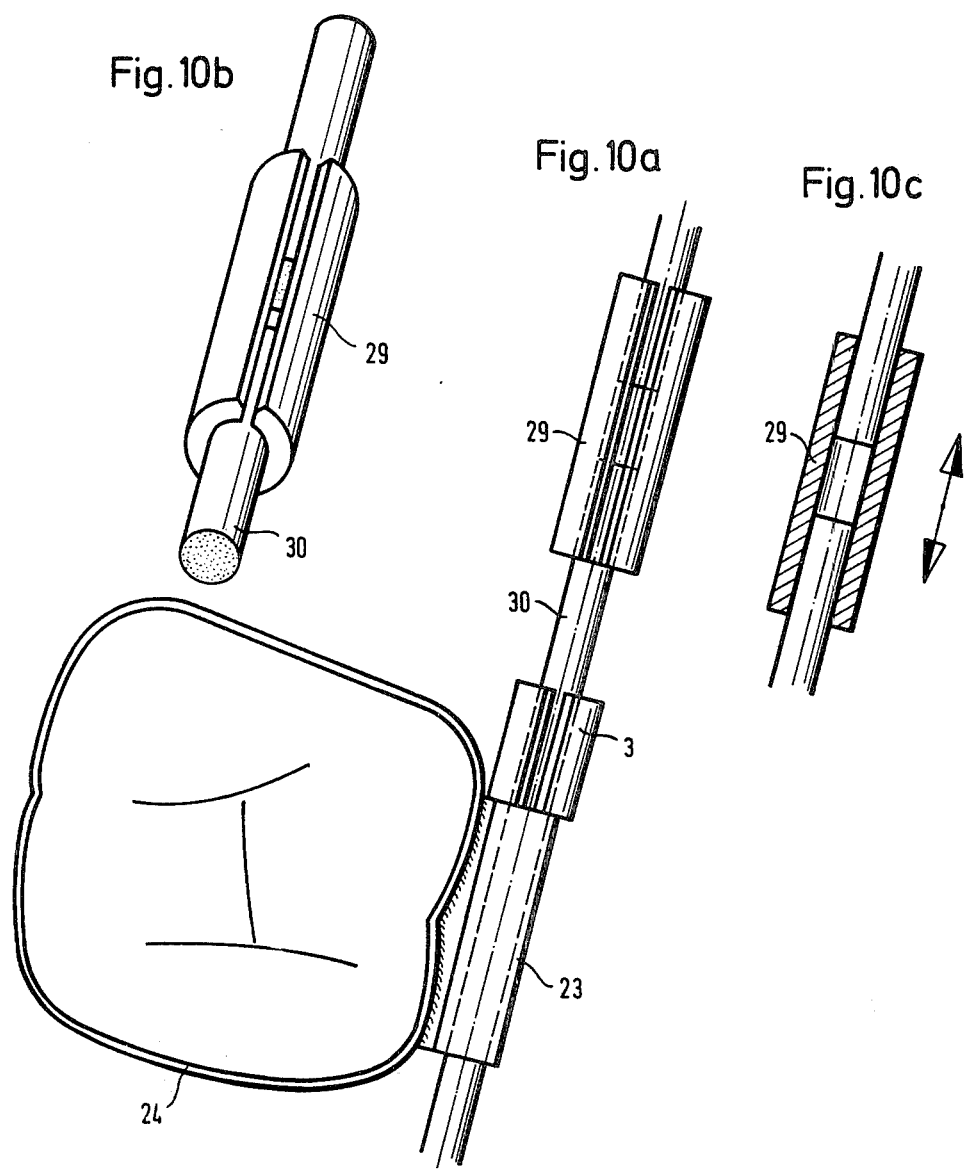

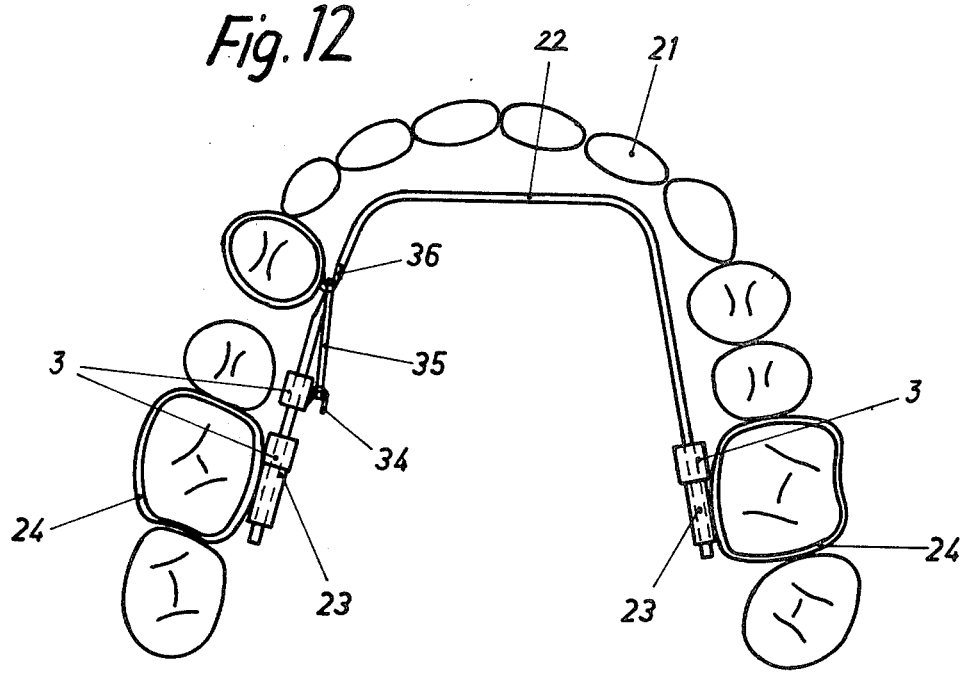

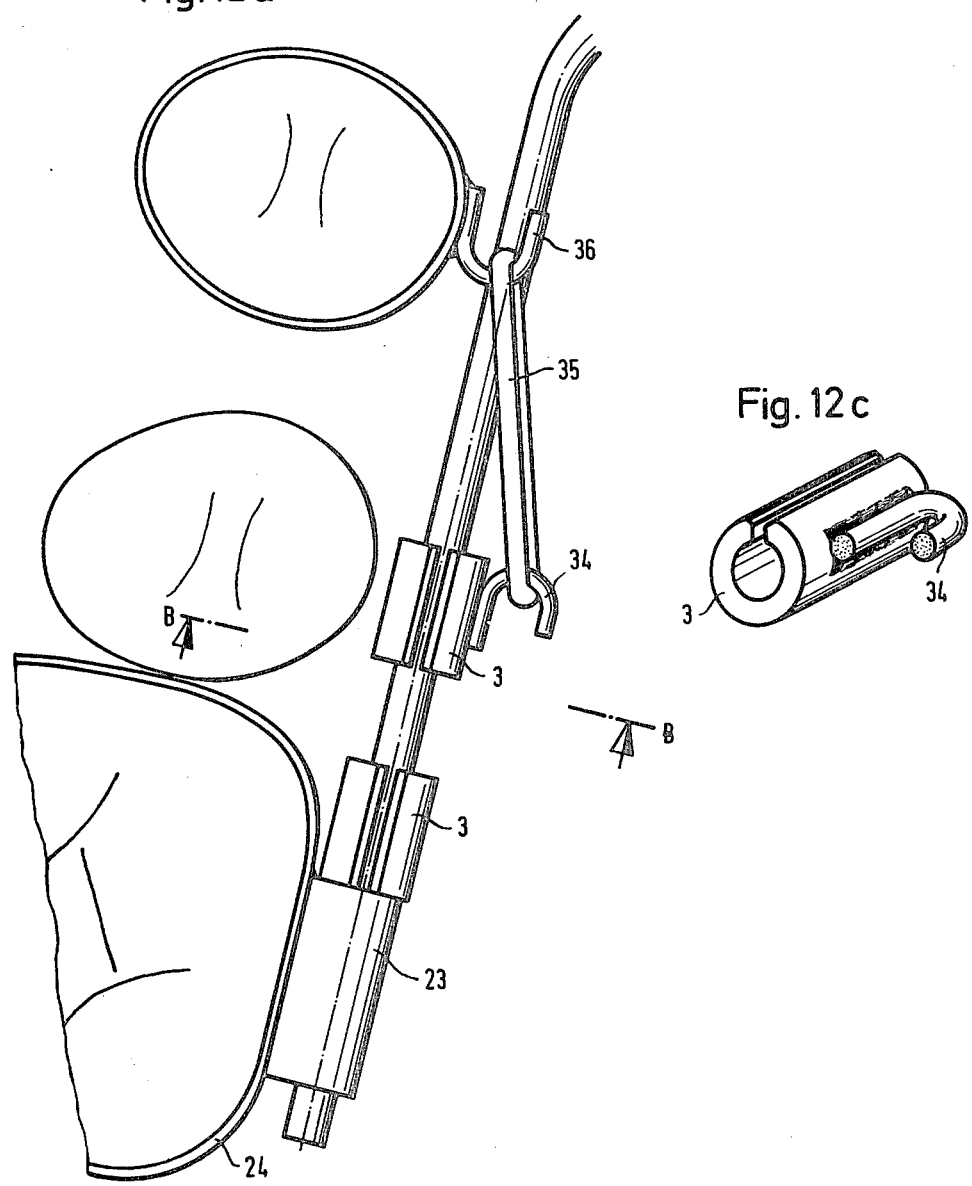

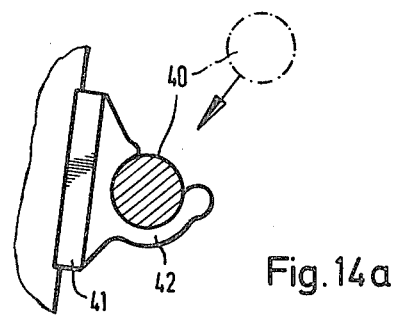
Fig. 14a
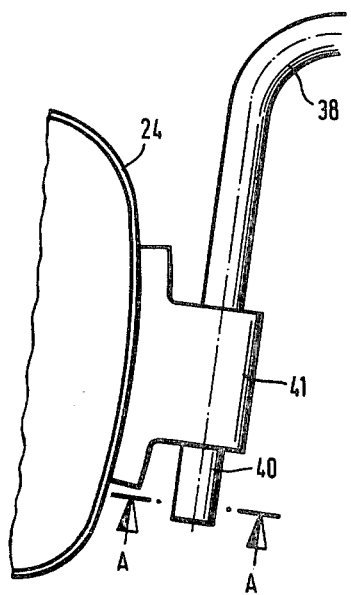
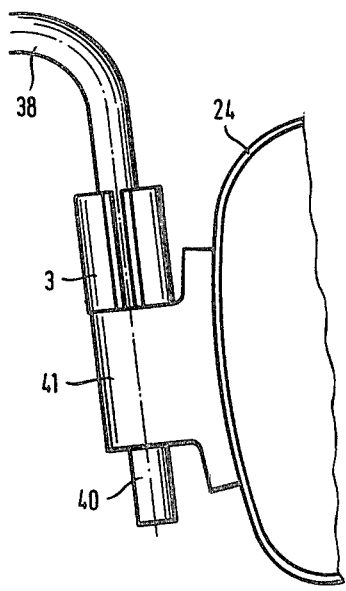
Fig. 13a

ORTHODONTIC APPLIANCE

This invention relates to an adjusting device for orthodontic appliances comprising an inner arch and at least one detachably connected tooth-connecting sleeve.

Orthodontic appliances having face arches which comprise an outer arch and an inner one require a stop, which is attached, e.g., at the end of the inner arch and controls the displacement of the molar tube provided with a tooth-connecting sleeve in the longitudinal direction in accordance with the desired correction. It is known to provide such stop by forming the end of the wire arch with a curved portion which extends away from the gum or by fixing a fit-on sleeve to said curved portion by welding or by means of transverse screws, which permits of an adjustment. The procedure is such that the face arch is adapted to the patient and the extent of the desired tooth correction is determined in the mouth. When the face arch has then been taken out of the mouth, the stops described above are mounted. As the correction proceeds, the stops must be readjusted. This procedure is complicated and time-consuming and sometimes requires the use of new parts.

It is an object of the invention to facilitate the adjustment and re-adjustment of the stop and to eliminate the need for a subsequent use of new parts and for a removal of the appliance when a re-adjustment is required.

In an adjusting device for orthodontic appliances comprising an inner arch and detachably connected tooth-connecting sleeves, this object is accomplished according to the invention in that a clamping sleeve formed with a radially inwardly tapering longitudinal slot resiliently clamps itself on the end of the inner arch and adapted to be widened at said slot to be slidable on the end portion of the wire arch. The clamping sleeve having a radially inwardly tapering longitudinal slot may be widened by pliers which have one jaw having a curved surface which is applied to one side of the clamping sleeve, and another jaw having a wedge part which is inserted into the longitudinal slot. The pliers are then operated to widen the clamping sleeve so that it is slidable on the end portion of the wire arch.

A further feature of the invention resides in that a round wire element is inserted in the tapering longitudinal slot of the clamping sleeve, and a closed fit-on sleeve is slidably fitted on the clamping sleeve, so that pressure can be applied to the fit-on sleeve over the wire element by pliers so as to widen the clamping sleeve and enable a sliding movement thereof.

It is a further object of the invention to provide clamping device of the kind described which enlarges the field of application of orthodontic appliances having inner arches. In connection with an orthodontic appliance having an inner arch which cooperates with guides on tooth-connecting sleeves provided on both sides and an associated correcting spring arch, this object is accomplished in that such clamping sleeves are arranged to form a stop which controls the initial stress of the spring arch.

According to further features of the invention the clamping device serves as a coupling or spreading element for orthodontic correcting arches or as an adjustable hook for connection to tension strips.

The state of the art as well as preferred illustrative embodiments of the invention are diagrammatically illustrated in the drawings and will be described hereinafter.

In the drawings,

FIG. 2a shows an enlarged portion of FIG. 2, describing in greater clarity the adjustable stop or the clamping sleeve.

FIG. 2b shows a partial sectional view of FIG. 2a taken along line B—B.

FIG. 2c shows an enlarged perspective view of the adjustable stop or clamping sleeve embracing the inner arch.

FIGS. 3 and 4 are perspective views showing two adjustable stops according to the invention.

FIGS. 5 and 6 show the use of pliers for adjusting the stops shown in FIGS. 3 and 4, respectively.

FIG. 5a shows an enlarged partial view of FIG. 5.

FIG. 5b shows FIG. 5a in a different position.

FIG. 8a shows a partial enlarged view of FIG. 8.

FIG. 8b shows a partial sectional view of FIG. 8a taken along line B—B.

FIG. 8c shows an enlarged perspective view of FIG. 8b.

FIG. 9a shows an enlarged exploded view of FIG. 9.

FIGS. 10 to 12 are top plan and detailed views showing different inner arches, and their adjustable straps.

FIG. 13a shows an enlarged partial and exploded view of FIG. 13.

FIG. 14a shows a partial sectional view of FIG. 13a taken along section line A—A, and also a different embodiment of the guide clip 42.

Figure 1:
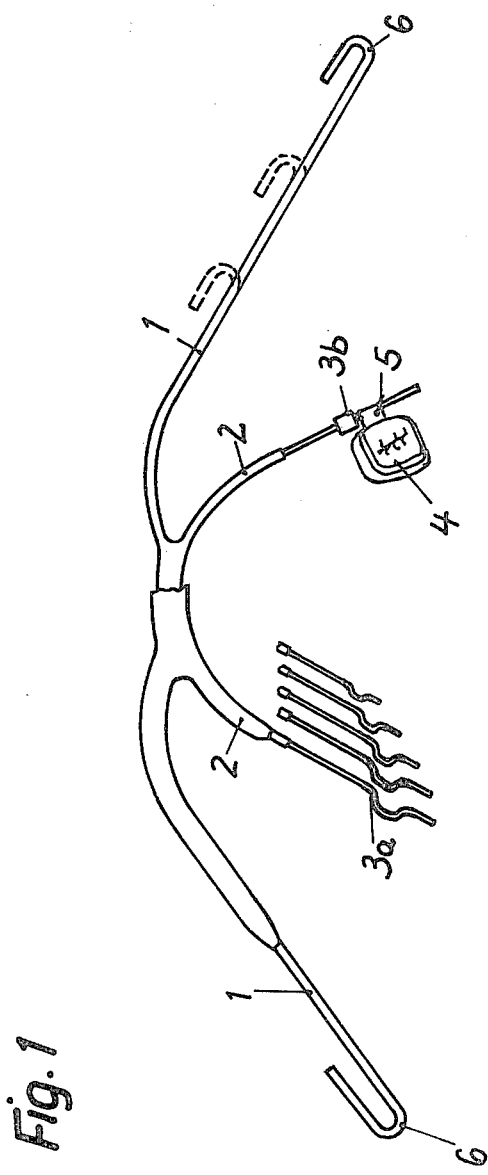
FIG. 1 shows a face arch provided with a known stop for controlling the tooth correction.

FIG. 1 of the drawings show two known orthodontic appliances comprising an extra-oral face arch or outer arch 1 and an oral tooth-jaw arch or inner arch 2. For correcting molar teeth, one of which is indicated at 4 on the right in FIG. 1, the inner arch 2 is provided with extensions, which are provided with tooth-connecting sleeves 5 which are connected to molar teeth such as 4 by tooth straps applied around respective teeth. The extensions of the inner arch are also provided with stops, which engage the tooth-connecting sleeves so as to control the correction. On one side, the stop consists of a bend 3a formed in the extension and extending away from the gums. On the other side, the stop consists of a stop sleeve 3b, which is fitted on and welded to the extension. Whenever the appliance is to be preset for a desired connection, the extensions provided with the stops 3a must be mounted or the stop sleeves 3b must be welded to the extensions and this must be altered whenever a re-adjustment is required. The end hooks 6 on the outer arch 1 serve for the connection to the nape strip with spring elements interposed, as is known per se.

Figure 2:
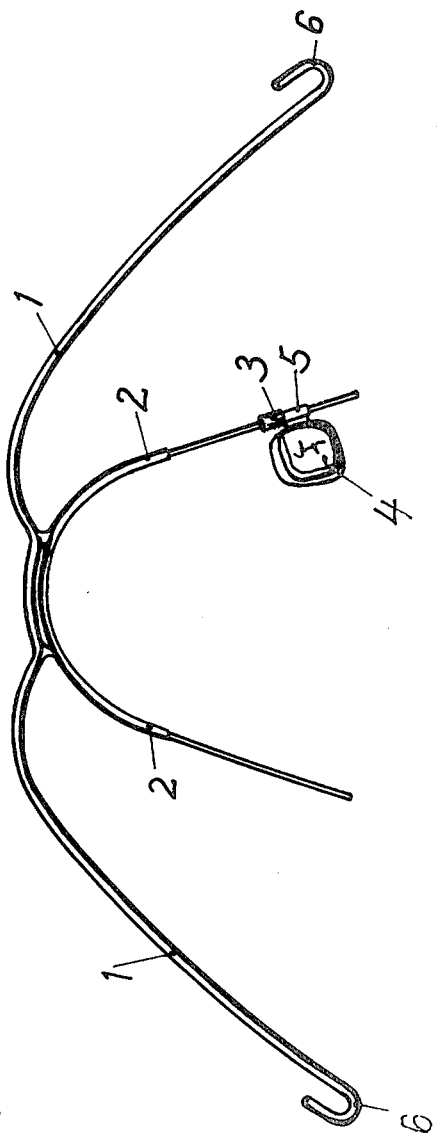
FIG. 2 shows a face arch provided with a correction-controlling stop according to the invention.

FIG. 2 shows an outer arch 1, and oral inner arch 2, and a clamping sleeve 3 according to the invention. The clamping sleeve serves as a stop for the tooth-connecting sleeve 5, which is connected to the tooth strap 5 applied around a molar tooth 4 that is to be corrected. FIG. 3 shows details of a clamping sleeve 3 in a simple embodiment, which has a wedge-shaped or a radially inwardly tapering longitudinal slot 7 and is fitted on the inner arch 2 from the free end thereof to serve as a stop in the manner shown in FIG. 2. The clamping sleeve 3 is operable by pliers 8 shown in FIG. 5. One jaw of the pliers 8 has a curved surface 9, which engages the clamping sleeve 3. The other jaw 10 has a wedge-shaped portion, which is inserted into the longitudinal slot 7. The pliers 8 are then operable to widen the clamping sleeve 3 so that it is slidably adjustable for presetting the desired tooth correction.

FIGS. 2a–2c show an enlarged and detailed description of clamping sleeve 3 and its relationship with the inner arch 2.

Figure 6:
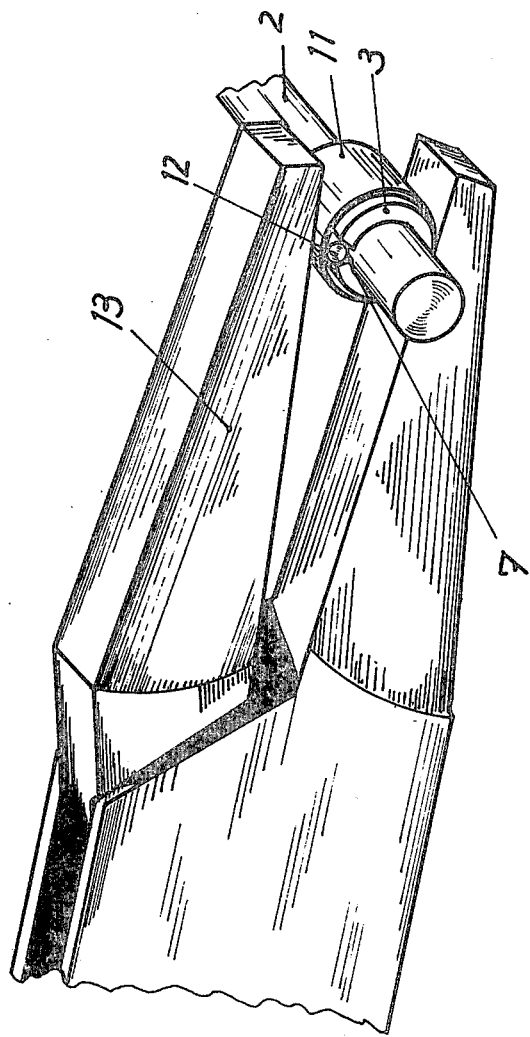

FIG. 4 shows also a clamping sleeve 3 which has a radially inwardly tapering longitudinal slot 7 and has been fitted on the inner arch 2 from its free end to act as a stop as in FIG. 2. A round wire element 12 has been inserted in the radially inwardly tapering slot 7 so as to protrude radially outwardly therefrom and a closed fit-on sleeve 11 has then been slidably fitted on the clamping sleeve 3. Pliers 13 can then be used to apply pressure as shown in FIG. 6 to enable a slidable adjustment of the clamping sleeve in the mouth so as to preset the appliance for the desired tooth correction.

FIGS. 5a and 5b show in great detail the operation of pliers 8 in widening the clamping sleeve 3.

Figure 7:
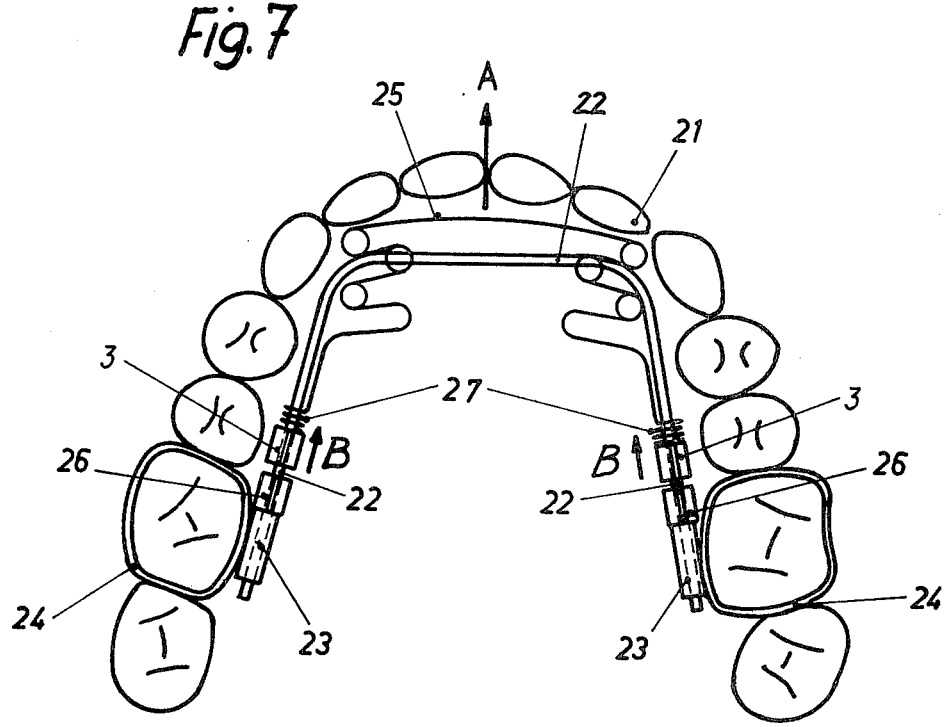
FIGS. 7 and 8 are top plan views showing inner arches provided with adjustable stops according to the inventin.
Figure 8:
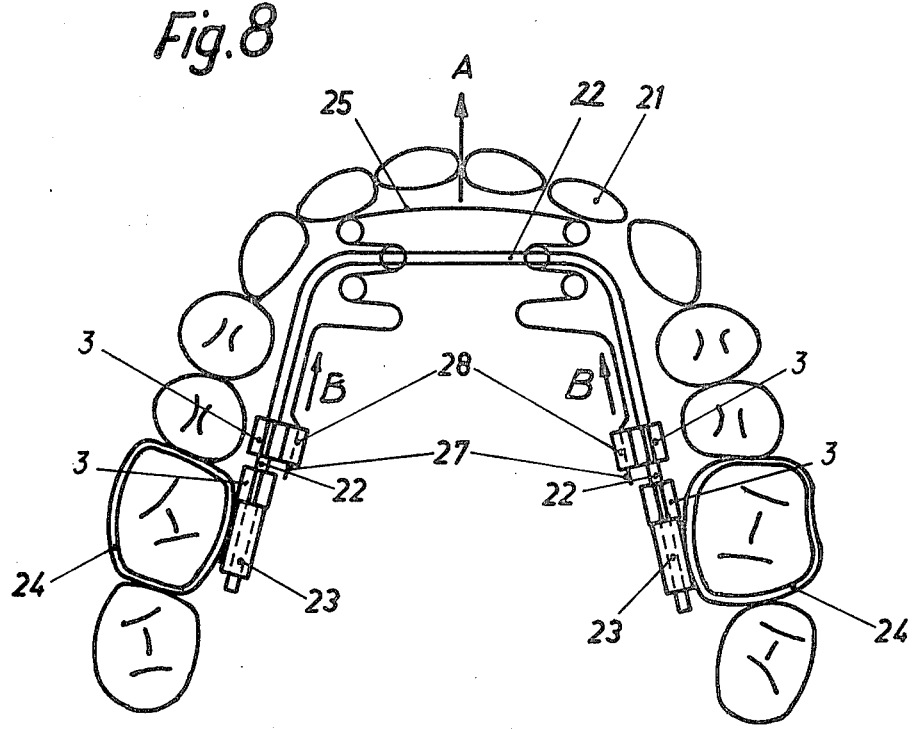

FIGS. 7 and 8 are top plan views showing a dental arch 21 and means for raising the forward teeth in the direction indicated by the arrow A. For this purpose an inner arch 22 of wire is provided, which is guided on both sides by tooth-connecting sleeves 23, which are connected to tooth straps 24. A correcting spring arch 25 is associated with the wire arch 22 and applies spring pressure to the forward teeth in the direction indicated by the arrow A. The spring arch 25 should be re-adjustable in dependence on the progress of the correction so that the complicated adaptation which has previously required is no longer necessary. This re-adjustment is enabled by the provision of two clamping sleeves 3 of the kind described hereinbefore. Two clamping sleeves 3 are disposed in a tandem arrangement between each tooth-connecting sleeve 23 and the adjacent end 27 or 27a of the correcting spring arch 25 so that the distance B can be altered to re-adjust the spring force acting in the direction of the arrow A.

Figure 9:
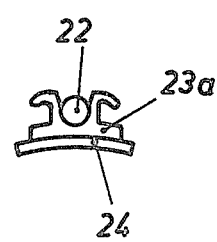
FIG. 9 is a top plan view showing a detail of the inner arches of FIGS. 7 and 8.

In the embodiment shown in FIG. 7, the ends 27 and 27a of the correcting spring arch 25 are slung around the wire arch 22 to cooperate with the clamping stop sleeves 3. FIG. 8 shows an embodiment in which the ends 27 of the correcting spring arch are fitted in tubular passages 28 formed in the clamping sleeves 3. In accordance with FIG. 9, each of the guides provided on the tooth-connecting sleeves 24 may constitute a clip 23a, so that an end portion of a wire arch 22 can be laterally inserted into and removed from such clip whereby the application and removal of the inner arch is much simplified and does not require a removal of the tooth straps 24.

FIGS. 8a–8c show in great detail the end 27 of the correcting spring arch being fitted in tubular passages 28 formed with the clamping sleeves 3 (in which inner arch 22 is fitted).

FIG. 9a shows an enlarged and exploded view of guid clip 23a which is a varied embodiment of sleeve 23.

FIG. 10 shows also an inner arch 22 which is applied to the dental arch 21. Clamping sleeves 3 of a first set serve as stops for tooth-connecting sleeves 23, which are connected to tooth straps 24 and serve to guide the inner arch 22. Longer clamping sleeves 29 of a second set connect sections 22a and 22b of inner arches to each other and to extensions 30.

FIGS. 10a–10c show in great detail the longer clamping sleeve 29 and its relationship to the sections of the inner arch 22a and 22b.

Figure 11:
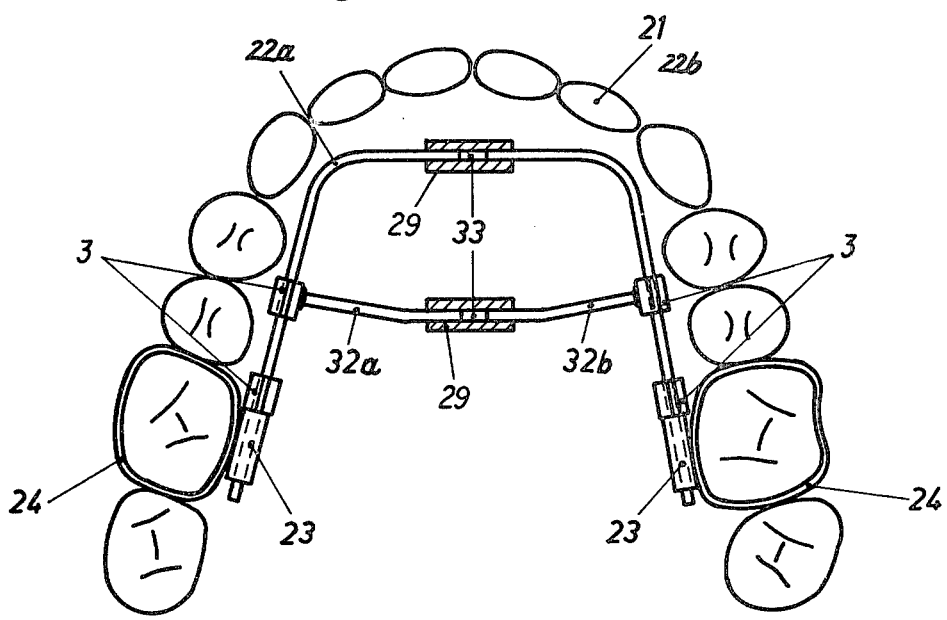

FIG. 11 shows an inner arch 22 comprising inner arch sections 22a, 22b and also shows longer clamping sleeves 29, one of which connects the inner arch sections 22a, 22b and the other of which connects two cross brace sections 32a, 32b, which are force-fitted in the clamping sleeve 29 and slidable relative thereto to permit of a spreading of the inner arch sections 22a, 22b. Air cushions 33 are left in the clamping sleeves 29 between the inner arch sections 22a, 22b and between the cross brace sections 32a, 32b and promote the spreading on the inner arch. In accordance with FIG. 12, a clamping sleeve 3 is provided with a hook 34, which is adjustable with the clamping sleeve and connected by an elastic tension strip 35 to a fixed hook 36, which is connected to a tooth to be corrected.

FIGS. 12a–12c show an enlarged portion of the orthodontic appliance of FIG. 12 illustrating in detailed, perspective, and sectional views, the relationship between clamping sleeve 3, hook 34, tension strip 35, hook 36, and inner arch 22.

Figure 13:
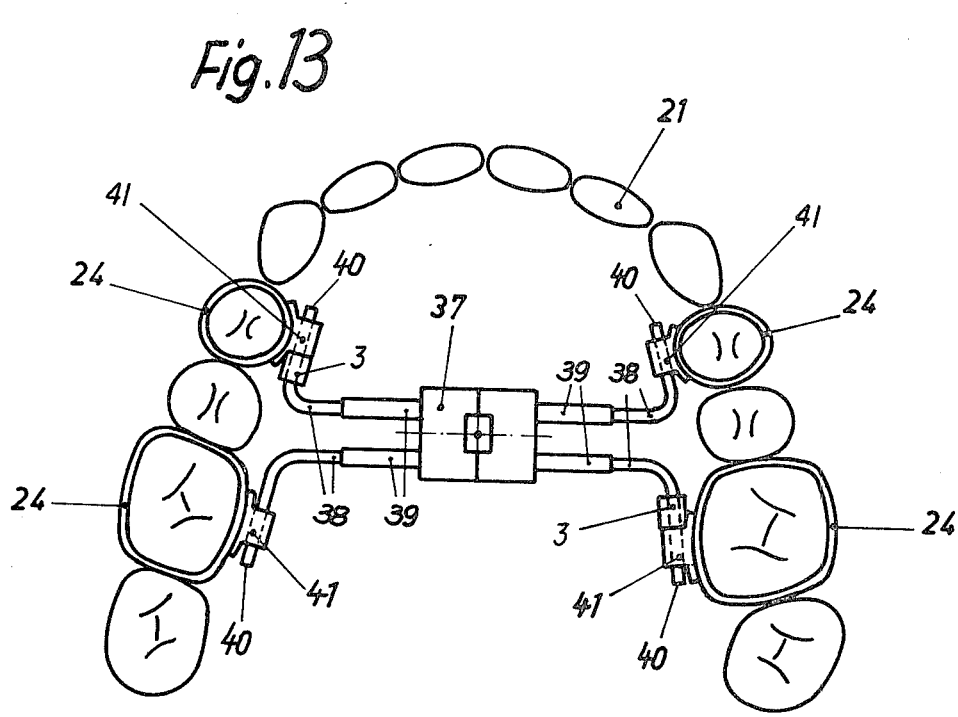
FIG. 13 is a top plan view showing an appliance for spreading a jaw.

FIG. 13 illustrates the use of clamping sleeves in connection with a spreading screw assembly 37 for effecting a palatinal split when the jaw is too narrow. Because the jaw is narrow, the movement of the screw assembly is limited because a large movement would require a long screw and this cannot be accommodated. Such palatinal split must be effected very soon, within a week, so that the parts of the jaw do not grow together too soon.

Figure 14:
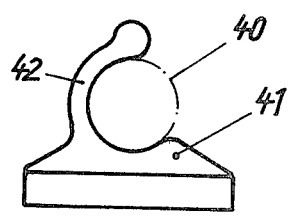
FIG. 14 is a top plan view showing a detail of FIG. 13.

FIG. 13 shows a spreading screw assembly 37 and a cross assembly consisting of four angled guide rods 38, which are held by clamping sleeves 3. The cross brace assembly is formed in that the four guide rods 38 are inserted at one end at 39 into the spreading screw assembly 37 and their angled arms 40 at the other end are connected to tooth-connecting sleeves 24 by means of respective guide clips 41. It is apparent from FIG. 14 that the guide clip 41 consists of a spring hook 42 of plastics material, which is provided on one side of the sleeve 24 and permits of a simple insertion and removal of the angled arms 40 of the cross brace assembly. This arrangement greatly facilitates the insertion of the cross brace assembly and the removal thereof for a re-adjustment or for the use of longer spreading screw assemblies 37.

FIG. 13a show an enlarged partial and exploded view of the embodiment of FIG. 13, illustrating the relationship between tooth connecting sleeve and guide clip 41, clamping sleeve 3, and angled arm 40.

FIG. 14a, there is shown a different embodiment of tooth connecting sleeve and guide clip 41, including guide clip 42 formed of plastic material. The angled arm 40 is being received in guide clip 42.

What is claimed is:

1. An orthodontic appliance for exerting a correcting force on at least one tooth of a patient, comprising an oral elongated inner arch, at least one tooth connecting sleeve adapted to be connected to a tooth of a patient and forming a guide for said inner arch, and at least one clamping sleeve which resiliently clamps itself on said inner arch, and engages said tooth connecting sleeve, said clamping sleeve having a radially inwardly tapering longitudinal slot, which is adapted to receive an implement, which implement is operable to widen said slot, so that said clamping sleeve is slidable along said inner arch.

2. An orthodontic appliance as set forth in claim 1, in which said tooth-connecting sleeve is provided with a clip, in which said inner arch is detachably held.

3. An orthodontic appliance as set forth in claim 1, in which a round-section wire element is inserted in and protrudes radially outwardly from said longitudinal slot and a closed fit-on sleeve is slidably fitted on said clamping sleeve over said wire element and is compressible to force said wire element deeper into said slot to widen the latter so that said clamping sleeve is slidable along said inner arch.

4. An orthodontic appliance as set forth in claim 1, in which said longitudinal slot is adapted to receive a widge-shaped implement, which is carried by pliers on one jaw thereof, the second jaw of said pliers having a concavely curved surface applicable to said clamping sleeve opposite to said longitudinal slot, so that said pliers are then operable to widen said longitudinal slot.

5. An orthodontic appliance as set forth in claim 1, further comprising said inner arch having sides and end portions on opposite sides of the patient's mouth, a correcting spring arch associated with said inner arch, and having opposite end portions, two tooth-connecting sleeves, which are adapted to be connected to teeth on opposite sides of the patient's mouth, and are in guiding engagement with respective end portions of said inner arch, and a first pair of said clamping sleeves mounted on said inner arch on respective opposite sides thereof, and which engage respective end portions of said correcting spring arch.

6. An orthodontic appliance as set forth in claim 5, in which the end portions of said correcting spring arch extend around said inner arch.

7. An orthodontic appliance as set forth in claim 5, in which each of said clamping sleeves has a first passage receiving said inner arch and a second passage receiving the adjacent end portion of said correcting spring arch.

8. An orthodontic appliance as set forth in claim 5, in which a second pair of said clamping sleeves are mounted on said inner arch on opposite sides thereof between respective ones of said tooth-connecting sleeves and respective clamping sleeves of said first pair, and engage respective ones of said tooth-connecting sleeves.

9. An orthodontic appliance as set forth in claim 1, in which said inner arch consists of first and second sections and said clamping sleeve resiliently clamps itself on said first and second sections, and is slidable along both said sections when said slot had been sufficiently widened.

10. An orthodontic appliance as set forth in claim 10, in which said first element consists of a first inner arch section said second element consists of a second inner arch section.

11. An orthodontic appliance as set forth in claim 9, in which said first and second sections of said inner arch define sealed air space in said clamping sleeve.

12. An orthodontic appliance as set forth in claim 9, in which a cross brace assembly is connected to said inner arch, and forms with said first and second sections a transverse brace assembly.

13. An orthodontic appliance as set forth in claim 1, in which said inner arch comprises a cross brace assembly which includes a spreading screw and is applicable to the patient's palate, two of said tooth-connecting sleeves are provided on opposite sides of said appliance, and two of said clamping sleeves are provided and connect said cross brace assembly to respective ones of said tooth-connecting sleeves.

14. An orthodontic appliance for exerting a correcting force on at least one tooth of a patient, comprising an elongated inner arch, at least one tooth-connecting sleeve adapted to be connected to a tooth of a patient, and provided on one side with a resilient clip of plastics material, for receiving the inner arch therein, and at least one clamping sleeve which resiliently clamps itself on said inner arch and engages said tooth-connecting sleeve, said clamping sleeve having a radially inwardly tapering longitudinal slot which is adapted to receive an implement for widening the same, so that said clamping sleeve is slidable along said inner arch.

15. An orthodontic appliance as set forth in claim 1, in which said inner arch comprises a cross brace.

16. An orthodontic appliance for exerting correcting forces on at least one tooth of a patient, comprising an elongated inner arch, at least one tooth-connective sleeve adapted to be connected to a tooth of a patient and in guiding engagement with said inner arch, and first and second clamping sleeves which resiliently clamp themselves on said elongated inner arch, and each of which has a radially inwardly tapering longitudinal slot, which is adapted to receive an implement which is operable to widen said slot so that said clamping sleeve is slidable along said elongated inner wire, said first clamping sleeve engaging said tooth-connecting sleeve, said second clamping sleeve carrying a hook which is engageable with an elastic strip adapted to be connected to another tooth of the patient and to exert a correcting force thereon.

17. An orthodontic appliance for exerting a correcting force on a tooth of a patient, comprising an elongated inner arch and a clamping sleeve which resiliently clamps itself on said elongated inner arch and has a radially inwardly tapering longitudinal slot, which is adapted to receive an implement which is operable to widen said slot so that said clamping sleeve is slidable along said elongated inner arch, said clamping sleeve carrying a hook which is engageable with an elastic strip adapted to be connected to a tooth of a patient and to exert a correcting force thereon.

18. An orthodontic appliance, for exerting correcting force on at least one tooth of a patient, comprising a cross brace assembly which is applicable to a patient's palate and includes a spreading screw assembly having opposite ends and two pairs of angled guide rods, said pairs of guide rods extending from opposite sides of said spreading screw assembly, two pairs of tooth-connecting sleeves disposed on opposite sides of said appliance and adapted to be connected to respective teeth of the patient, each of said tooth-connecting sleeves being connected to one of said guide rods, and at least one pair of clamping sleeves, which resiliently clamp themselves on respective ones of said guide rods, and engage respective ones of said tooth-connecting sleeves, and each of which has a radially inwardly tapering longitudinal slot which is adapted to receive an implement, said implement being operable to widen said slot so that each of said clamping sleeves is slidable along a respective one of said guide rods.

19. An orthodontic appliance as set forth in claim 19, in which each of said tooth-connecting sleeves is provided on one side with a resilient clip of plastics material for receiving a respective one of said guide rods.

20. An orthodontic appliance as set forth in claim 18, in which two pairs of clamping sleeves are provided, and each of said tooth-connecting sleeves is connected to one of said guide rods by one of said clamping sleeves.

21. An orthodontic appliance as set forth in claim 18, in which a round section wire element is inserted and protrudes radially outwardly from said longitudinal slot, and a closed fit-on sleeve is slidably fitted on each of said clamping sleeves, over said wire element, and is compressible to force said wire element deeper into said slot, to widen the latter, so that each of said clamping sleeves is slidable along a respective one of said guide rods.

22. An orthodontic appliance for exerting a correcting force on at least one tooth of a patient, comprising an oral elongated inner arch, a tooth connecting sleeve adapted to be connected to a tooth of the patient, and provided on one side with a resilient clip of plastics material, said inner arch being received in said clip, and at least one clamping sleeve which resiliently clamps itself on said inner arch and engages said tooth-connecting sleeve, said clamping sleeve having a wedge-shaped longitudinal slot which is adapted to receive an implement, which is operable to widen said slot, so that said clamping sleeve is slidable along said inner arch.

* * * * *